(12) United States Patent
Tallentire et al.

(10) Patent No.: US 6,553,848 B1
(45) Date of Patent: Apr. 29, 2003

(54) SAMPLING DEVICES

(75) Inventors: Alan Tallentire, Wilmslow (GB); Colin Samuel Sinclair, Manchester (GB)

(73) Assignee: Air Dispersions Ltd., Manchester (GB)

( * ) Notice: Subject to any disclaimer, the term of this patent is extended or adjusted under 35 U.S.C. 154(b) by 128 days.

(21) Appl. No.: 09/589,101

(22) Filed: Jun. 8, 2000

(30) Foreign Application Priority Data

Jun. 9, 1999 (GB) .............................................. 9913443

(51) Int. Cl.7 ................................................. G01N 1/00
(52) U.S. Cl. .................. 73/864.81; 73/863.41
(58) Field of Search ........................... 73/28.01, 863.41, 73/863.43, 863.51–863.56, 863.58, 863.61, 864.33, 864.81, 865.5, 863.81, 863.82, 863.86

(56) References Cited

U.S. PATENT DOCUMENTS

| 3,498,027 A | 3/1970 | Buchtel, Jr. |
| 4,942,774 A | 7/1990 | McFarland |
| 4,946,650 A * | 8/1990 | Rothele .................... 73/863.58 |
| 4,998,954 A * | 3/1991 | Burr ......................... 73/863.58 |
| 5,537,879 A * | 7/1996 | Malczewski et al. .... 73/863.58 |

FOREIGN PATENT DOCUMENTS

| EP | 316 688 | 5/1989 |
| EP | 428 850 | 5/1991 |
| JP | 4-143632 | 5/1992 |

* cited by examiner

Primary Examiner—Robert Raevis
(74) Attorney, Agent, or Firm—Leydig, Voit & Mayer, Ltd.

(57) ABSTRACT

A sampling device samples gas from a gas stream flowing through a tube to means utilizing the gas to detect the presence or otherwise of particulate contaminants. The device ensures that the sampled flow has at least as many particulate contaminants/unit volume as the main flow. The device divides the flow into two parallel flows and then decelerates one flow before providing the sampled flow. The other flow passes to the utilizing means. The device is particularly useful in the sterile packaging of product to detect microorganisms and other culturable contamination.

26 Claims, 6 Drawing Sheets

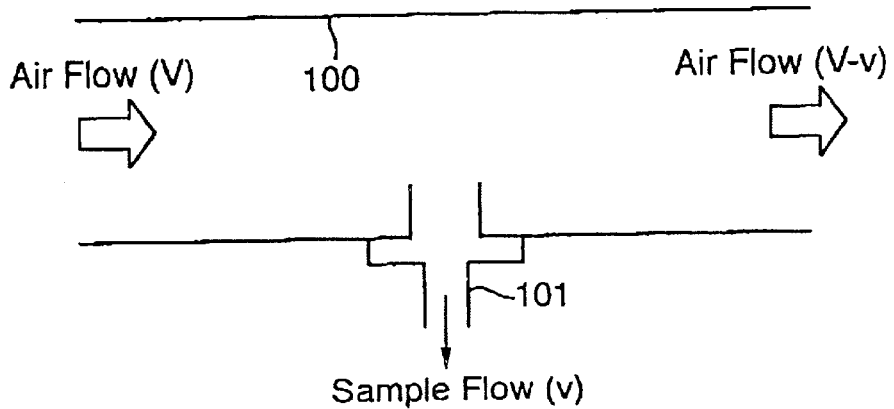
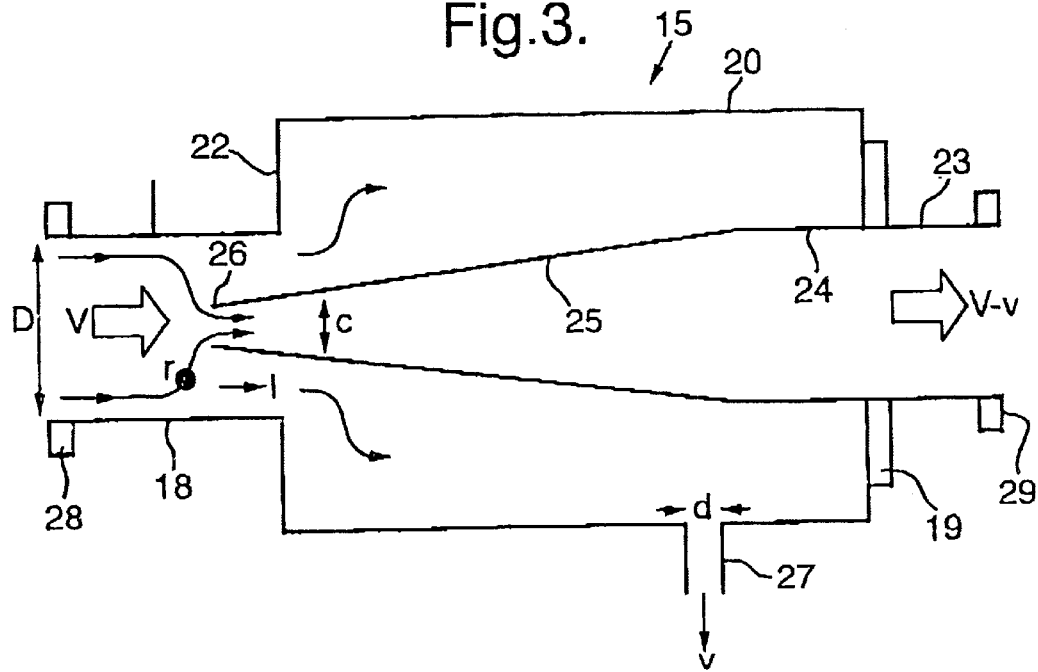

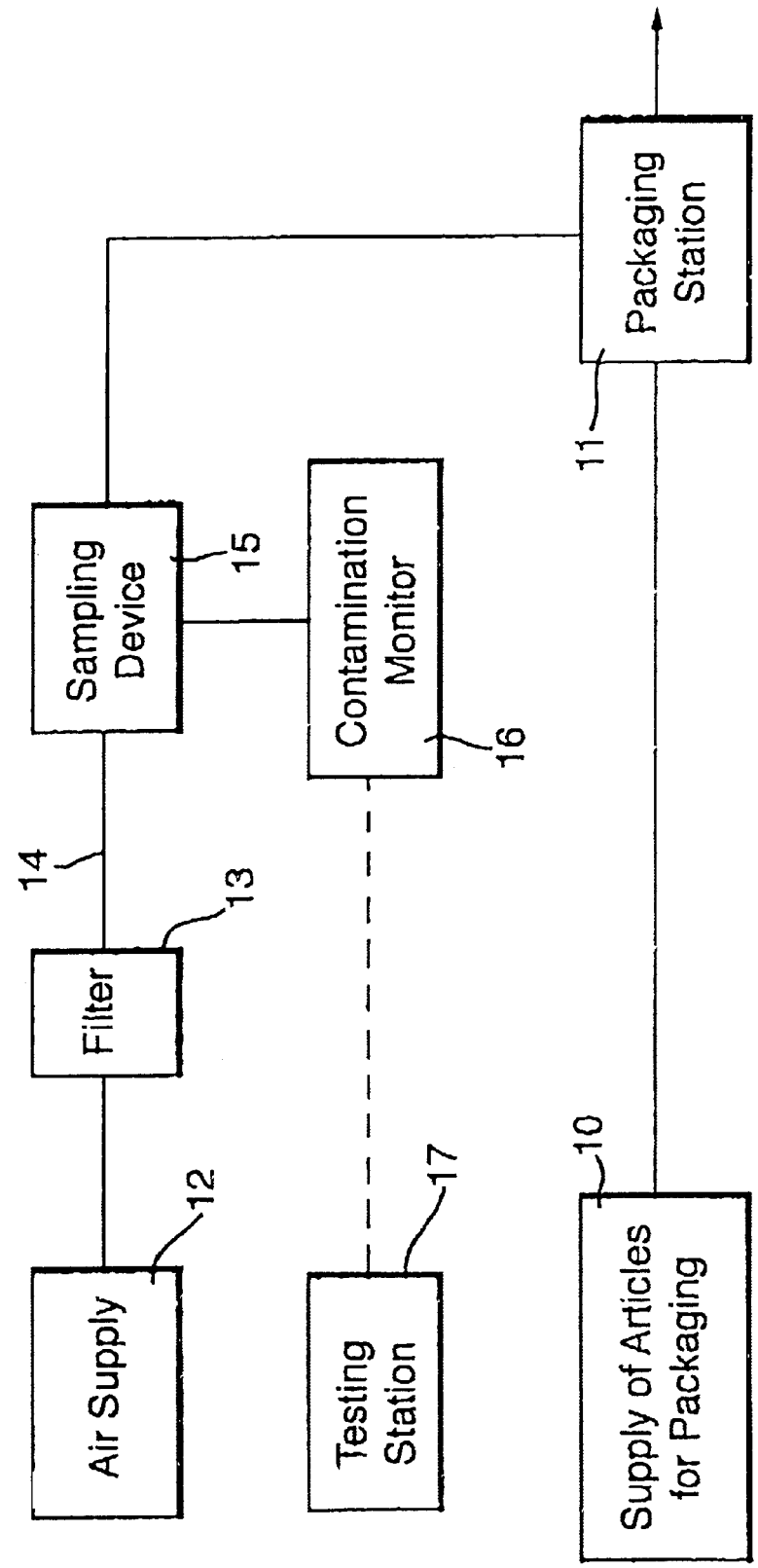

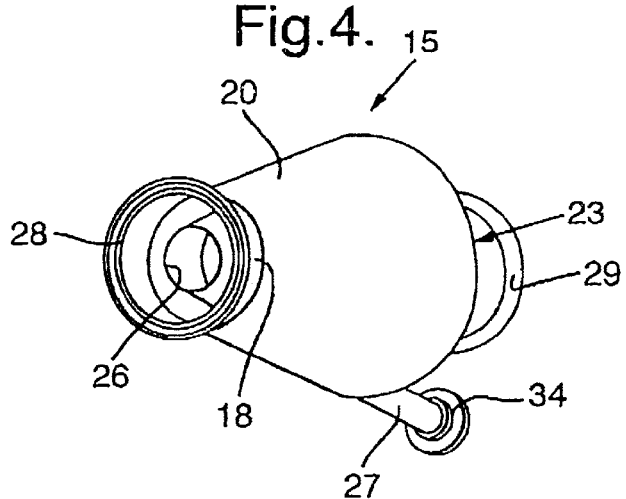
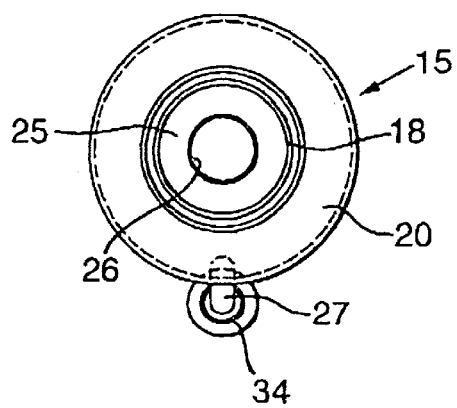
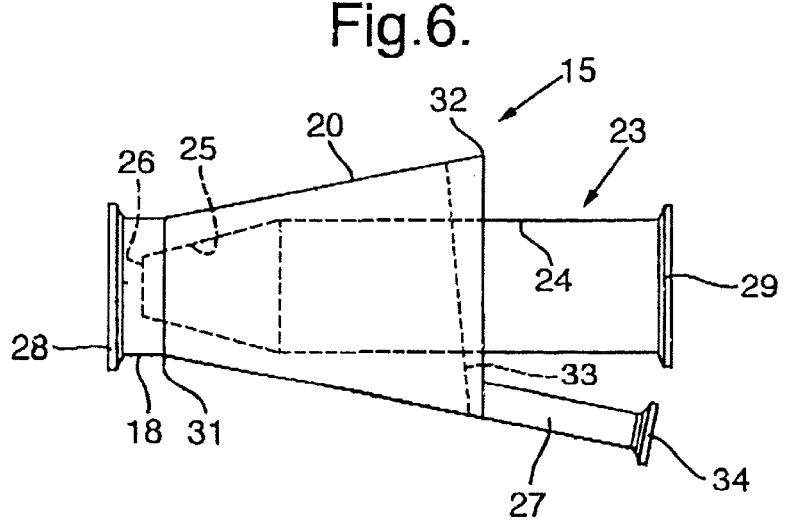

SAMPLING DEVICES

BACKGROUND TO THE INVENTION

1. Field of the Invention

The invention relates to sampling devices and to air supply systems incorporating such devices and sterile filling apparatus including such air supply systems.

2. Brief Review of the Prior Art

There are many circumstances where gas from a gas stream is flowed through a tube from a source to means utilizing the gas and where the gas may contain unwanted particulate contamination. An example of this is sterile filling apparatus such as blow/fill/seal apparatus where the gas is air and is used to prevent contamination in the sterile packaging of articles such as sterile liquids. Plainly, the presence in the air of particulate contaminants such as micro-organisms can compromise the sterility of the packaging process and may result in packaged product being contaminated.

In order to remove contamination, the air supply is normally filtered through a filter (such as HEPA or 0.2 μm rated filter) having a rating sufficient to remove unwanted particulate contaminants such as micro-organisms. The filter can be inspected at the end of its life to see whether its integrity has been compromised to allow contaminants to enter the air stream supplied to the apparatus. This procedure may, however, render a large quantity of the articles unusable if it is found that the filter integrity has been compromised, since it is not possible to say when during the life of the filter the compromise occurred so making it necessary to remove all articles produced during the life of the filter.

In order to try and overcome this problem, it has been proposed to include in the tube a sampling port in the form of a pipe extending through a wall of the tube normal to the length of the tube. This port is connected to a unit containing a filter which filters out all particulate contaminants in a sample airstream taken from the port. At intervals, the port is closed and the unit removed so that any particulate contaminants on the filter material can be identified. In the case of biological materials, this may be done by culturing. If an unacceptable level of contaminants is present, the batch of articles produced with a contaminated airstream can be identified and removed.

FIG. 1 shows a sampling port of this known type inserted in a tube. Referring to FIG. 1, the tube 100 is of generally constant circular cross-section along its length and passes air from a source to apparatus utilizing the air. A sampling port 101 is inserted in the tube with the port extending normal to the axis of the tube. Air flows through the sampling port to a unit containing a filter as described above. At intervals, the port is closed and the unit removed so that any particulate contaminant on the filter material can be identified.

It is a problem with a sampling port of this known type that it does not always reliably identify the presence of particulate contaminants. There can be occasions when sampled air shows no contaminants but replacement of the filter element at the end of the filter element life shows the integrity of the filter to have been compromised so allowing contaminated air to pass to the article. It is then necessary to remove from production all the articles made during the life of the filter. This is plainly unsatisfactory.

SUMMARY OF THE INVENTION

According to a first aspect of the invention, there is provided a sampling device for sampling gas from a gas stream flowing from a source to means utilizing said gas to determine the presence of particulate contamination comprising a pipe through which the gas stream is flowed, a flow divider receiving the gas stream from the pipe and separating the gas stream into first and second flows, the first flow passing to said gas utilizing means and the second flow passing to a contamination detector for determination of particulate contaminants per unit volume present in the gas stream and comprising a deceleration volume disposed downstream of the flow divider and arranged to decelerate the second flow before the second flow exits for contamination detection.

By arranging the flows in accordance with the first aspect of the invention, a gas sample is obtained for analysis which will reveal reliably the presence of particulate contaminants.

According to a second aspect of the invention, there is provided a sampling device for sampling gas from a gas stream flowing from a source to means utilizing said gas to determine the presence of particulate contamination comprising an inlet tube through which the gas stream is flowed, a housing for receiving a portion of the gas flowing through the inlet tube, and an exit pipe for receiving another portion of the gas flowing through the inlet pipe, wherein the housing includes an outlet for connecting to a contamination sampling means and wherein the volume of the housing is such as to decelerate the portion of the gas received therein.

According to a third aspect of the invention, there is provided a sampling device for sampling gas from a gas stream flowing from a source of gas to means utilizing the gas to determine the presence of particulate contamination comprising a housing for receiving and decelerating a portion of the flow, an exit tube for conveying the remainder of the flow and a sampling tube leading from the housing for connection to contamination detection means.

According to a fourth aspect of the invention, there is provided an air supply system comprising a source of air, a filter supplied with air from said source, an outlet passage for conveying filtered air from the filter to means utilizing said air, the outlet passage including a sampling device according to the first, second or third aspects of the invention.

According to a fifth aspect of the invention, there is provided a sterile packaging apparatus for packaging articles comprising an air supply system according to the fourth aspect of the invention, the outlet passage leading to a filling and sealing station of the apparatus.

According to a sixth aspect of the invention, there is provided a method of sampling an air stream to test for the presence of particulate contaminants comprising dividing the air stream into first and second flows, decelerating the first flow, passing decelerated first flow to contamination detection means and passing the second flow for utilization.

The following is a more detailed description of some embodiments of the invention, by way of example, reference being made to the accompanying drawings in which:

BRIEF DESCRIPTION OF THE DRAWINGS

FIG. 1 is a cross-section of a sampling port inserted in a tube,

FIG. 2 is a schematic view of a sterile packaging apparatus incorporating a sampling device, FIG. 3 is a cross section of a first form of sampling device for use in the apparatus of FIG. 2, FIG. 4 is a perspective view from one end of a second form of sampling device for use in the apparatus of FIG. 2, FIG. 5 is an end elevation of the sampling device of FIG. 4, FIG. 6 is a side elevation of the sampling device of FIG. 5.

DESCRIPTION OF THE PREFERRED EMBODIMENT

Figure 7:
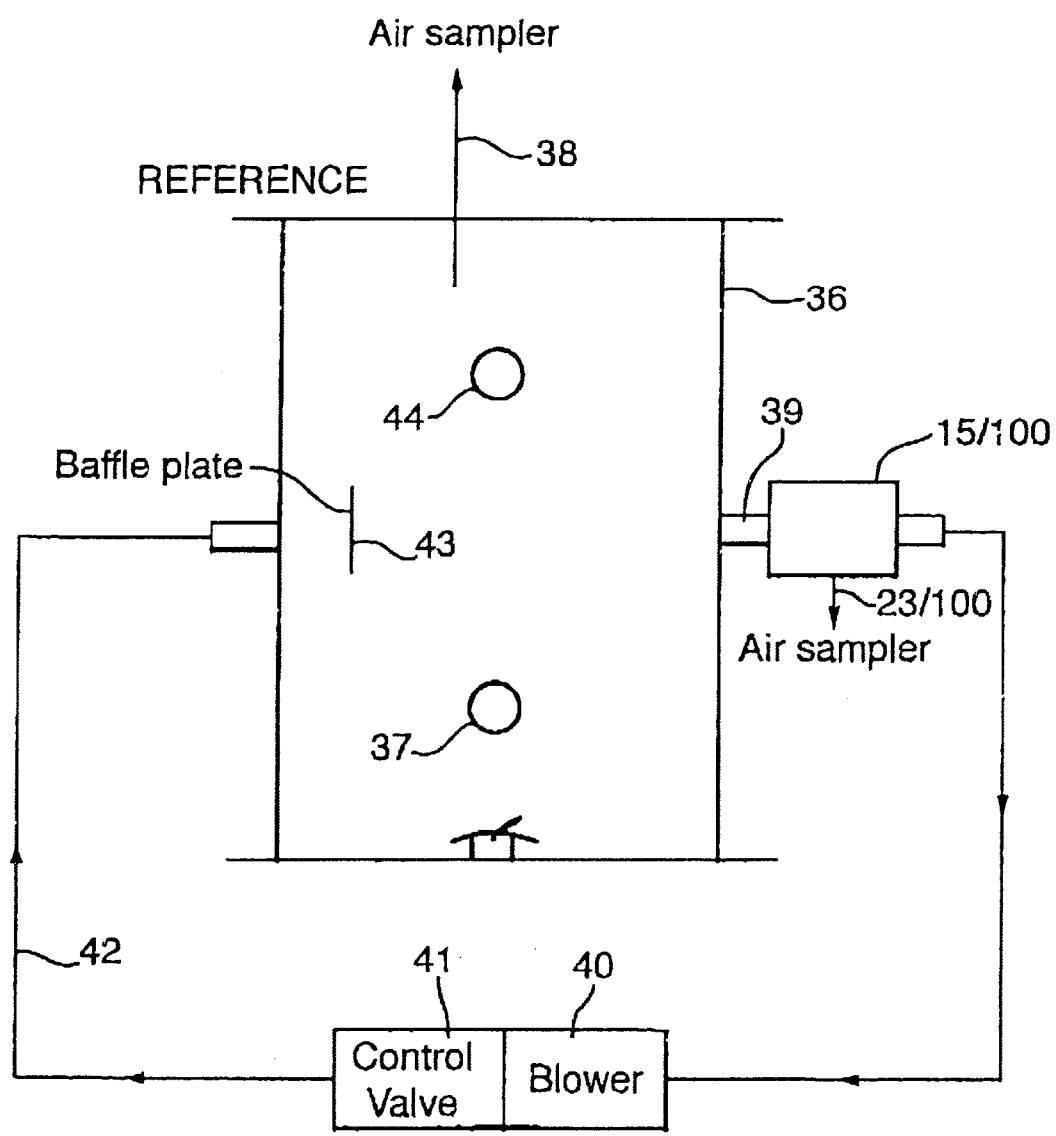
FIG. 7 is a schematic view of a test rig for testing the efficiency of the sampling port of FIG. 1 and the sampling device of FIGS. 4 to 6.

Referring first to FIG. 2, the sampling device will be described in the context of its use in a sterile packaging apparatus in the form of a blow/fill/seal apparatus. It will be appreciated, however, that the sampling device can be used in other apparatus and the following description is by way of example only.

Referring to FIG. 2, the blow/fill/seal apparatus includes a supply 10 of product to be packaged which may typically be a sterile liquid. The product is fed to a packaging station 11 where a plastics material is blown into an appropriately shaped packaging, product is fed to the packaging and is then sealed in the packaging. For example, a bottle for receiving liquid may be blown at the packaging station 11, sterile liquid placed in the bottle and the bottle sealed.

The blowing, filling and sealing must take place in a sterile atmosphere and, for this purpose, air is supplied to the packing station 11 from an air supply 12. Air from the supply 12 is fed to an appropriately rated filter 13 which removes particulate contaminants in the air. For example, the filter may have an absolute rating of 0.2 μm. From the filter 13, filtered air is supplied through a pipe 14 to the packing station 11.

A sampling device 15, examples of which will be described below, is inserted in the pipe 14 and feeds a sample of the air to a contamination monitor 16, again to be described in detail below. A collection device from the contamination monitor 16 is taken to a testing station 17 to test for the presence of contamination.

Testing takes place at predetermined time intervals which are correlated with the production of packaged articles from the packaging station 11 so that if contamination appears, it is known which batch of articles has been packaged using contaminated air.

Referring next to FIG. 3, the first form of sampling device 15 comprises an inlet tube 18 of constant circular cross section along its length. This connects to an aperture in a first end wall 19 of a circular cross-section tube forming a housing 20 whose axis is coaxial with the axis of the inlet tube 18. The opposite second end wall 22 of the housing 20 carries an exit tube 23. The second end wall 22 is provided with reinforcing plate to mount the exit tube 23. The exit tube 23 has an outlet portion 24 of constant circular cross-section along its length and extending through the second end wall 22 of the housing 20. This leads to an inlet portion which is of reducing circular cross section as it extends away from the outlet portion 24 to terminate in an inlet 26. The exit tube 23 is coaxial with the axes of the inlet tube 18 and the housing 20 and, as seen in FIG. 2, the inlet 26 and the associated inlet portion form an inner tube lying within the inlet tube 18.

The housing 20 is also provided with a sampling tube 27. The sampling tube 27 extends from the curved outer surface of the housing 20 and is located closer to the second end wall 22 of the housing. The sampling tube 27 is of circular cross-section with its axis normal to the axis of the housing 20.

The free end of the inlet tube 18 and the outlet portion 24 of the exit tube 23 are provided with respective flanges 28,29 to allow them to be connected in the pipe 14 between the filter 13 and the packaging station 11. The sampling device 15 may be made of stainless steel to allow it to be steam sterilized in situ.

In use, the sampling device 15 of FIG. 2 is inserted in the pipe 14 utilizing the flanges 28,29. Air from the filter 13 passes to the inlet tube 18 and the inlet tube 26 acts as a flow divider to divide the air with a first portion of the air taken from the centre of the pipe 14 flowing into the exit tube 23 and a second portion of the air taken from adjacent the wall of the pipe flowing into the housing 20. As will be seen, the division is such that the flows are initially parallel. It will be appreciated that the proportion of air flowing into the housing 12 as compared with the proportion of air flowing to the exit tube 23 is determined by the relative cross sections of the inlet tube 18, the inlet 26 to the exit tube 23 and the sampling tube 27 and so, in turn, depend on the diameter (D) of the inlet tube 18, the diameter (a) of the inlet 26 of the exit tube 23, and the diameter (d) of the sampling tube 27. It has been found that satisfactory sampling can be achieved when the air flow between the sampling tube is between 1×10$^{-2}$ and 2×10$^{-2}$ of the air flow through the inlet tube 18. For example, typical air flows through the inlet tube 18 may be 1.3 m$^3$min$^{-1}$ and 1.8 m$^3$mm$^{-1}$ with a flow through the sampling tube of 11 dm$^3$mm$^{-1}$.

The second flow of air enters the housing 20 and, because of the larger volume of the housing 20, is decelerated so causing contaminants in the air flow also to be decelerated. The air/contaminants in the housing 20 then pass to the sampling tube 27. The sampling tube 27 is connected to the contamination monitor 16. This may comprise, in known fashion, a filter material (not shown) through which the air from the sampling tube 27 passes. After a predetermined period of time, the sampling tube 27 is closed, the filter material removed from the contamination monitor 16 (with care being taken not to contaminate the material) and the material taken to the testing station 17 for analysis. There, the filter material is used as a culture medium and any contamination in the form of microorganisms or other culturable biological material present is cultured and examined. If contamination has occurred, then the apparatus is stopped until the source of the contamination is discovered and those articles packaged between the last negative test and the positive test are removed for destruction.

An alternative form of the sampling device will now be described with reference to FIGS. 4 to 6. In FIGS. 4 to 6, parts common to FIG. 3, on the one hand, and to FIGS. 4 to 6, on the other hand, are given the same reference numerals and will not be described in detail.

Referring now to FIGS. 4 to 6, the second form of sampling device has an inlet tube 18 of constant circular cross-section along its length with a flange 28 at its free end. The housing 20 is, however, frusto-conical with a smaller diameter end 31 leading from the inlet tube 18 and a larger diameter end being closed by a wall 33 lying in a plane angled to the axis of the housing 20. An outlet portion 24 of an exit tube 23 passes through this wall 33 and terminates at its outer end in a flange 29. The outlet portion 24 is of circular cross-section along its length and leads to an inlet portion 25 of frusto-conical shape and an inlet 26. The inlet 26 and the associated inlet portion 25 form an inner tube within the outer tube 18. The cone angle of both the housing 20 and the inlet portion 25 is about 13° in order to maintain laminar flow across these surfaces.

A sampling tube 27 leads from the wall 33 and has its axis parallel to but spaced from the intersection with the housing 20 of a plane including the housing axis and the sampling pipe axis. The sampling tube 27 terminates in a flange 34.

The sampling device of FIGS. 4 to 6 is used in the same way as the sampling device of FIG. 3. The sampling tube 27 is connected to the contamination monitor 16 by a pipe attached to the sampling tube 27 utilizing the flange 34.

The sampling device of FIGS. 4 to 6 may also be made of stainless steel so that it can be steam sterilized in situ.

As indicated above, the purpose of sampling the air is to detect the presence in the air of contamination, particularly microorganisms. It is therefore a requirement of the sampling device 15 that air passing through the sampling tube 27 has at least the same amount of contaminants per unit volume as the air leaving through the exit tube 23.

In this regard, it will be appreciated that there is no significant disadvantage in the air passing through the sampling tube 27 having a higher amount of contamination per unit volume than the air in the exit tube 23. Indeed, this could be an advantage in making it easier to determine the presence of such contamination, particularly when levels are low.

In order to test the effectiveness of the sampling device of FIGS. 4 to 6 in this regard, use was made of the test rig shown in FIG. 7.

Referring now to FIG. 7, the test rig comprises a dispersion chamber 36 having an inlet 37 connected to a Collison nebulizer. The nebulizer is of a known kind and is not illustrated or described in further detail. The nebulizer produces in the chamber a mist from a liquid containing in suspension a known microorganism, described in more detail below.

The chamber 36 has a first outlet line 38 connected to an air sampler (not shown) which measures the number of microorganisms per unit volume in air taken from the chamber 36. The second outlet line 39 leads to an air sampler, which may be either the sampling device 15 described above with reference to FIGS. 4 to 6 or the sampling port of FIG. 1. The exit tube 23 of the sampling device of FIGS. 4 to 6 or the tube 100 of the sampling port leads to a blower 40 whose output is controlled by a control valve 41 connected to a return pipe 42 leading to the chamber 36. A baffle plate 43 is located opposite the end of the return pipe 42 in the chamber 36 so that incoming air impinges on the baffle plate 43.

An air outlet 44 is connected to the atmosphere via a high efficiency filter (not shown) to ensure that air exhausting from the chamber 36 is free of microorganisms.

The following Examples use the test rig of FIG. 7.

EXAMPLE 1

A sampling device 15 as described above with reference to FIGS. 4 to 6 was connected to the second outlet line 39 of the chamber 36.

The Collison nebulizer was charged with an aqueous suspension of the bacterial endospore *Bacilllus subtilis* var.niger (BS) having an aerodynamic size of about 1.3 $\mu$m. This was nebulized by the Collison nebulizer and fed into the chamber 36. The control valve 41 was adjusted to give an air flow through the second outlet line 39 of about 1.3 $m^3 min^{-1}$. At the same time, air was passed to the sampler and a count made of the number of viable organisms of BS per unit volume ($N_s$). The second outlet line 39 and the proportions of the inlet tube 18, the inlet 26 and the sampling tube 27 were such as to provide a sampling rate air flow through the sampling tube 27 of about 11 $dm^3 min^{-1}$. The number of viable organisms of BS per unit volume ($N_{ST}$) of the sampled air was then counted. The efficiency of the sampling device 15 was then calculated as $$\frac{N_{ST}}{N_s} \times 100\%$$

This was repeated a number of times and average efficiency ($E_{SD}$) calculated.

The sampling device 15 was then replaced with the sampling port 100 of FIG. 1 and a similar average efficiency ($E_{SP}$) derived as described above.

Figure 8:
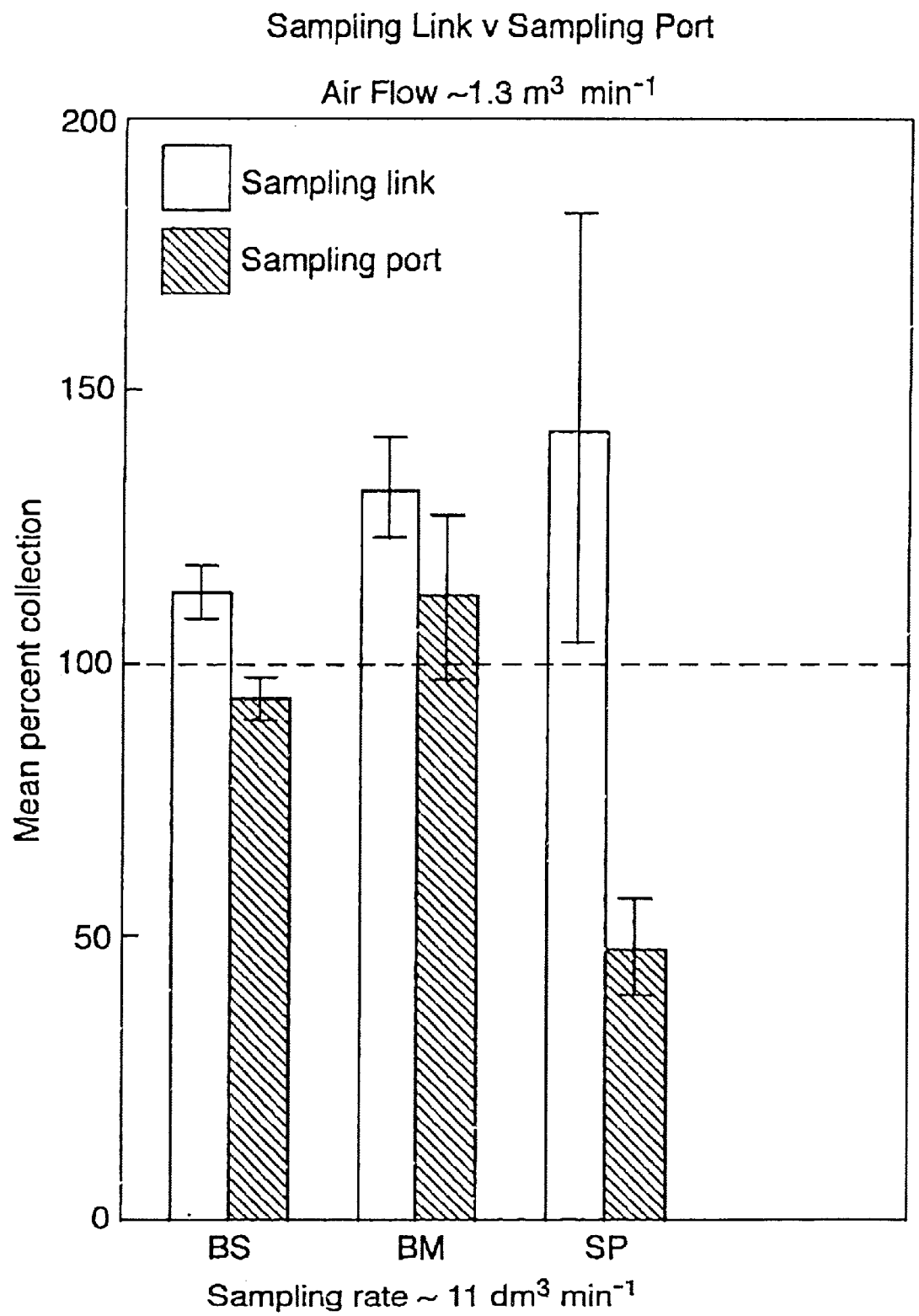
FIG. 8 is a bar chart showing the efficiency of collection of three (BS, BM, SP) different sizes and types of particulate contaminants with a total air flow of 1.3 m$^3$min$^{-1}$ and an air flow of 11 dm$^3$min$^{-1}$ to the sampling port of FIG. 1 and the sampling device of FIGS. 4 to 6.

FIG. 8 is a bar chart showing above the designation BS $E_{SD}$ (plain bar) and $E_{SP}$ (shaded bar) using BS at the air flow of about 11 $dm^3 min^{-1}$. Also shown as a straight vertical line at the top of each bar is an indication of the range of efficiencies measured.

EXAMPLE 2

As Example 1 but using the bacterial endospore *Bacillus megaterium* KM (BM) having an aerodynamic size of about 1.6 $\mu$m. The measured average efficiencies are $E_{SD}$ and $E_{ST}$ shown as bars on FIG. 8 above the designation BM with the range of efficiencies being shown by vertical lines.

EXAMPLE 3

As Example 1 but using the yeast cell *Schizosaccharomyces pombe* (SP) having an aerodynamic size of about 6.7 $\mu$m. The measured average efficiencies are $E_{SD}$ and $E_{SP}$ shown as bars on FIG. 8 above the designation SP with the range of efficiencies being shown by vertical lines.

EXAMPLE 4

Figure 9:
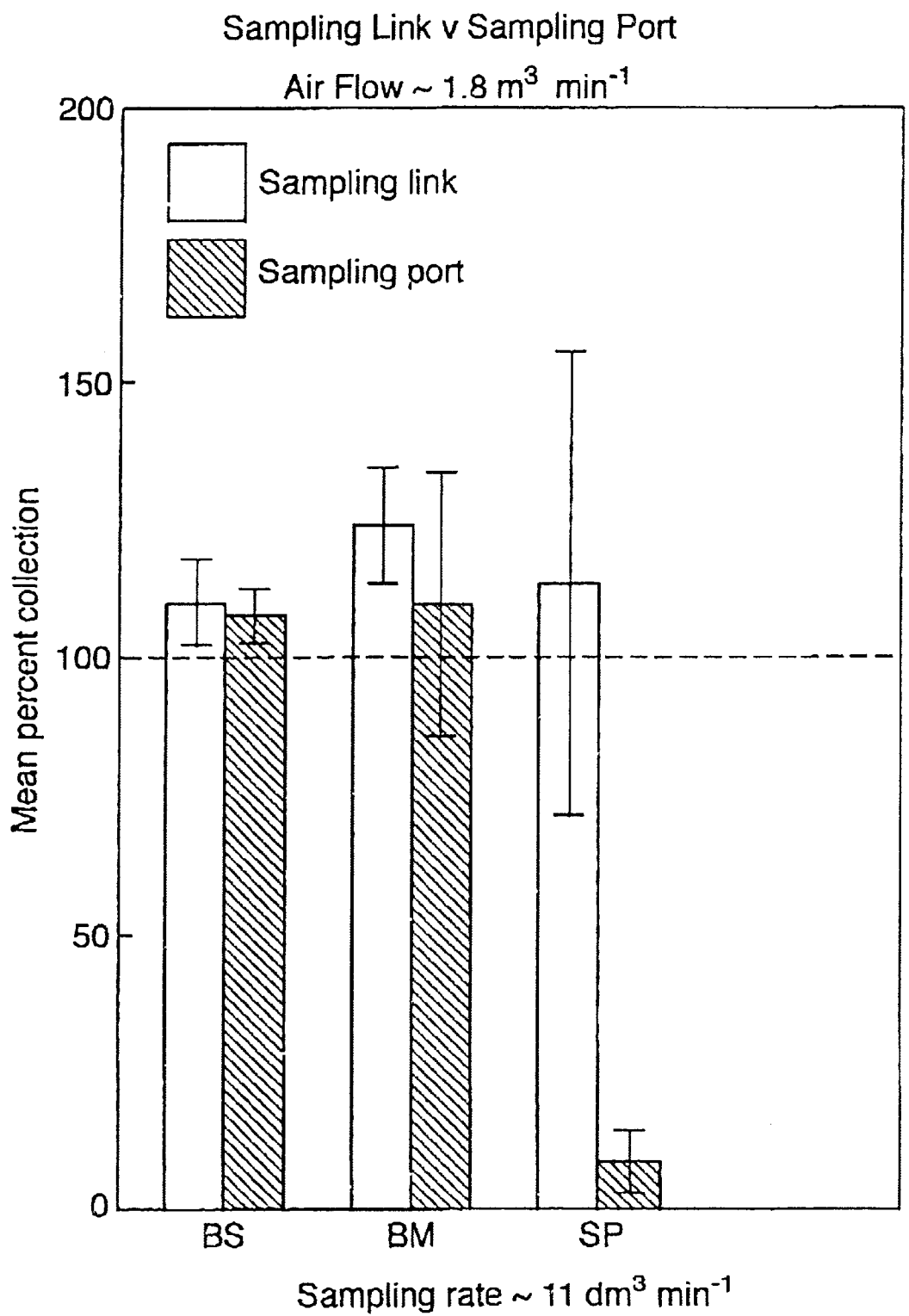
FIG. 9 is a bar chart showing the efficiency of collection of 3 (BS,BM,SP) different sizes and types of particulate contaminants with a total air flow of 1.8 m$^3$min$^{-1}$ and an air flow of 11 dm$^3$min$^{-1}$ to the sampling port of FIG. 1 and the sampling device of FIGS. 4 to 6.

As Example 1 but with a flow through the second outlet line 39 of 1.8 $m^3 min^{-3}$. The results are shown in FIG. 9 in a similar way to FIG. 8 as bars ($E_{SD}$-plain bar, $E_{SP}$-shaded bar) together with vertical lines indicating the range of efficiencies measured.

EXAMPLE 5

As Example 2 but with a flow through the second outlet line 39 of 1.8 $m^3 min^{-1}$. The measured average efficiencies are $E_{SD}$ and $E_{SP}$ shown as bars on FIG. 9 with the range of efficiencies being shown by vertical lines.

EXAMPLE 6

As Example 3 but with a flow through the second outlet line 39 of 1.8 $m^3 min^{-1}$. The measured average efficiencies are $E_{SD}$ and $E_{SP}$ shown as bars on FIG. 9 with the range of efficiencies being shown by vertical lines.

The results of these Examples will now be discussed.

At a sampling rate of 11 $dm^3 min^{-1}$, the sampling link 15 gave average efficiencies consistently above 100%. This means that, for all three contaminants, the sampling air contained at least as much contaminant per unit volume as the air flow through the sampling device. This means that any detection of contaminants from the sampled air will represent the presence of contaminants in the air flow through the exit pipe 23.

In contrast, the sampling port 101 provided efficiencies of greater than 100% only with the BS and BM bacterial endospores. When the size of the contaminant increased with the yeast cell SP, the sampling port 101 gave an efficiency of significantly less than 100%. At an air flow of 1.8 $m^3min^{-1}$, the efficiency was very significantly below 100%. This means, that when used to sample contaminants in air, this sampling port may indicate that no contamination is present when, in fact, significant contamination is present. This may lead to the sale of products which are not packed in a sterile fashion or, if when the filter is changed it is seen to be compromised, it may require the destruction of very significant amounts of a possibly non-sterile product.

This finding is more significant as a result of a study of particles including microorganisms in air. This found a mean aerodynamic size of around 19 $\mu$m. Accordingly, many of the particles to be detected by the sampling device will be at least 6.7 $\mu$m in size and plainly it is the ability to detect such larger particles that is important. Thus the sampling port 101 of FIG. 1 can be expected to produce unreliable results in normal usage.

Although not certain, it is believed at the present time that this may be due to the fact that, in the sampling port 101 of FIG. 1, it is necessary for particles flowing through the pipe 100 to turn through 90° if they are to enter the sampling tube 101. Larger particles, in particular, will have an inertia which will tend to cause them to continue travelling along the pipe 100 even if the airstream which is conveying them is turning to exit through the sampling tube 101. Accordingly, air entering the sampling tube 101 does not contain a representative volume of such larger particles.

In the sampling device of FIGS. 4 to 6, on the other hand, the particles are not diverted as they leave the entry pipe. Indeed, due to the flow patterns provided by the location of the inlet 26 of the exit tube 24 within the inlet tube 18, while the majority of the air may pass into the exit pipe 23, at least as many particulate contaminants per unit volume are present in the air passing into the housing 20 as are present in the first flow of air passing through the exit tube 24. Once in the housing 20, the velocity of the particles decreases significantly and so inertia has less effect on the particles. This means that air leaving through the sampling tube 27 contains at least as many particulate contaminants per unit volume as the air in the housing 20.

It will be seen from FIGS. 8 and 9 that the sampling device of FIGS. 4 to 6 increases its efficiency as the particle size increases with an air flow of 1.3 $m^3min^{-1}$. This may be evidence that, as particle sizes increase further, the efficiency will rise even higher. This may be important when the amount of contaminant per unit volume is low to make detection more certain.

The sampling port 101 of FIG. 1 requires suction in order to draw air from the pipe 100. As described above, the sampling port 101 must be closed in order for a test to be conducted for particulate contaminants. When this is done, if there is any leak around the sample port 101, air flowing through the pipe 100 may create a Venturi effect which will draw air into the pipe 100 through the leak. In this way, contaminated air may be drawn into the pipe 100 and will not be detected in air taken from the sampling port 101.

In the sampling devices 15 of FIGS. 3 to 6, there is always a positive pressure in the housing 20 even when the sampling tube 27 is closed. This positive pressure ensures that no air is drawn into the housing 20 if there is any leak in the sampling tube 27 or its couplings.

As shown in FIG. 1, it is preferred to have the sampling tube 27 leading vertically downwardly to the contamination monitor 16. This ensures that contaminants in the air flow freely to the contamination monitor 16 and do not get trapped in bends and junctions.

It will be appreciated that the embodiments of the sampling device 15 shown in FIGS. 3 to 6 are examples of the way in which the sampling device 15 may be embodied in accordance with the principles of the invention. Both sampling devices described above with reference to FIGS. 2 to 5 show a portion of the air in the inlet tube 18 in a path parallel to the exit tube 23 before sampling. This may be achieved in ways other than as described above. The various tubes and pipes are described as being of circular cross-section, this need not necessarily be the case.

In addition, they provide a housing which decelerates the sampled air before passing it to the sampling tube. This ensures that inertial effects in larger particles do not distort the air taken by the sampling tube 27 for analysis.

Another example of sterile packaging apparatus in which the sampling device 15 may be used is form/fill/seal apparatus where sterile solid products such as powders, pills, dressings and medical devices are packaged into plastics trays formed at the packing station 11 and then sealed.

What is claimed is:

1. A sampling device for sampling gas from a gas stream flowing from a source to means utilizing said gas to determine the presence of particulate contamination comprising a pipe through which the gas stream is flowed; a flow divider receiving the gas stream from the pipe and separating the gas stream into first and second flows, the first flow passing to said gas utilizing means and the second flow passing to a contamination detector for determination of the number of particulate contaminants per unit volume present in the gas stream; and comprising a deceleration volume disposed downstream of the flow divider and arranged to decelerate the second flow before the second flow exits for contamination detection.

2. A device according to claim 1 wherein the first flow is taken from the centre of the pipe and the second flow from a space between the centre of the pipe and the pipe.

3. A device according to claim 2 wherein said flow divider comprises an inlet tube and an inner tube located within the inlet tube, the inlet tube being contiguous with said pipe.

4. A device according to claim 3 wherein the inner tube includes a portion of increasing cross-sectional area, in the direction of flow of the gas stream.

5. A device according to claim 4 wherein said portion is an initial portion of the inner tube, in the direction of flow of the gas stream.

6. A device according to claim 5 wherein said initial portion of the inner tube leads to a portion of constant cross-section along the length thereof.

7. A device according to claim 4 wherein the inner tube is of circular cross-section.

8. A device according to claim 1 wherein the first and second flows are initially parallel.

9. A device according to claim 1, further comprising a housing downstream of the flow divider, the housing defining the volume such as to decelerate the second flow.

10. A device according to claim 9 wherein the housing comprises a tube downstream of the flow divider of increased cross-section relative to the cross-section of the inlet tube.

11. A device according to claim 10 wherein said flow divider comprises an inlet tube and an inner tube located within the inlet tube, the inlet tube being contiguous with said pipe and connected to the housing.

12. A device according to claim 11 wherein the housing has a cross-section that increases along the length thereof.

13. A device according to claim 12 wherein the cross-section of the housing is circular.

14. A device according to claim 11 wherein the housing terminates in an end wall that extends between the housing and the inner tube.

15. A device according to claim 9 wherein the housing includes an outlet for connection to said contamination detector.

16. A device according to claim 15 wherein the outlet comprises a pipe.

17. A device according to claim 16 wherein the flow provided by the flow divider, the volume of the housing and the cross-section of the outlet pipe are such as to produce a positive pressure in the housing to prevent the ingress of outside air.

18. An air supply system comprising a source of air, a filter supplied with air from said source, an outlet passage for conveying filtered air from the filter to means utilizing said air, the outlet passage including a sampling device according to claim 1.

19. A sterile packaging apparatus for packaging product comprising an air supply system according to claim 18, the outlet passage leading to a filling and sealing station.

20. An apparatus according to claim 19 wherein the apparatus is a blow/fill/seal apparatus or a form/fill/seal apparatus.

21. An apparatus according to claim 19 wherein the sampling device is made of a material that is steam sterilizable in situ.

22. An apparatus according to claim 21 wherein the sampling device is made of stainless steel.

23. A sampling device for sampling gas from a gas stream flowing from a source to means utilizing said gas to determine the presence of particulate contamination comprising an inlet tube through which the gas stream is flowed, a housing for receiving a portion of the gas flowing through the inlet tube, and an exit pipe for receiving another portion of the gas flowing through the inlet tube, wherein the housing includes an outlet for connecting to contamination sampling means and wherein the volume of the housing is such as to decelerate the portion of the gas received therein.

24. A device according to claim 23 wherein the amount of gas fed to said housing, the volume of said housing, and the flow of gas from the outlet are such as to produce a positive pressure in the housing to prevent the ingress of outside air.

25. A sampling device for sampling gas from a gas stream flowing from a source of gas to means utilizing the gas to determine the presence of particulate contamination comprising a housing for receiving and decelerating a portion of the flow, an exit tube for conveying the remainder of the flow and a sampling tube leading from the housing for connection to contamination detection means.

26. A method of sampling an air stream to test for the presence of particulate contaminants comprising dividing the air stream into first and second flows, decelerating the second flow, passing the decelerated second flow to contamination detection means and passing the first flow for utilization.

* * * * *